United States Patent [19]
Gaskill et al.

[11] Patent Number: 5,379,109
[45] Date of Patent: Jan. 3, 1995

[54] METHOD AND APPARATUS FOR NON-DESTRUCTIVELY MEASURING LOCAL RESISTIVITY OF SEMICONDUCTORS

[75] Inventors: D. Kurt Gaskill, Alexandria; Nicholas Bottka; Alok K. Berry, both of Burke, all of Va.

[73] Assignee: The United States of America as represented by the Secretary of the Navy, Washington, D.C.

[21] Appl. No.: 899,977

[22] Filed: Jun. 17, 1992

[51] Int. Cl.⁶ .................. G01N 21/55; G01N 21/84
[52] U.S. Cl. ............................... 356/445; 356/432
[58] Field of Search .......... 356/445, 326, 318, 432, 356/432 T, 30, 447, 448, 328; 250/227.23

[56] References Cited

U.S. PATENT DOCUMENTS

| | | | |
|---|---|---|---|
| 4,211,488 | 7/1980 | Kleinknecht | 356/369 |
| 4,273,421 | 6/1981 | Gurtler | 350/353 |
| 4,581,939 | 4/1986 | Takahashi | 73/643 |
| 4,750,822 | 6/1988 | Rosencwaig et al. | 356/445 |
| 4,758,092 | 7/1988 | Heinrich et al. | 356/364 |
| 4,854,710 | 8/1989 | Opsal et al. | 356/432 |
| 4,893,084 | 1/1990 | Rau | 324/341 |
| 4,953,983 | 9/1990 | Bottka et al. | 356/445 |
| 5,042,952 | 8/1991 | Opsal et al. | 356/432 |

FOREIGN PATENT DOCUMENTS

409271 1/1991 European Pat. Off.

OTHER PUBLICATIONS

"Novel Contactless electroreflectance spectroscopy of semiconductors"—Gal et al.; Applied Physics letters, 56(6) 5 Feb. 1990.

*Primary Examiner*—Richard A. Rosenberger
*Assistant Examiner*—LaCharles Keesee
*Attorney, Agent, or Firm*—Thomas E. McDonnell; Charles J. Stockstill

[57] ABSTRACT

An apparatus for non-destructively measuring resistivity of a semiconductor, such as InP, comprises light sources for illuminating a preselected portion of the semiconductor with first and second light beams, each of a preselected single wavelength, the first light beam operating to excite the semiconductor by photo injecting carriers, and the second light beam bombarding the local portion of the semiconductor with a preselected photon energy. The apparatus measures a fractional change in reflectance of the second light beam responsive to the first light beam, and records this fractional change in reflectance for various values of photon energy of the second light beam, to generate a photoreflectance line-shape. The photoreflectance line-shape is used to calculate a photoreflectance line-shape phase angle, which is used to determine the resistivity of the preselected portion of the semiconductor.

20 Claims, 6 Drawing Sheets

METHOD AND APPARATUS FOR NON-DESTRUCTIVELY MEASURING LOCAL RESISTIVITY OF SEMICONDUCTORS

BACKGROUND OF THE INVENTION

1. Field of the Invention

The present invention relates generally to non-destructive measurement of local resistivity of semiconductors and, more particularly, to non-destructive measurement of local resistivity of semi-insulating InP substrates.

2. Description of the Related Art

The technology for manufacturing high-speed electronic and optoelectronic devices from periodic table group III-V materials has reached the stage where cost reduction through mass production techniques is the immediate goal. To maximize the effectiveness of mass production methods, non-destructive, automated evaluations need to be implemented throughout the manufacturing process. This is especially true for those device structures grown on semi-insulating (SI) InP substrates. The performance of these device structures, especially for the case of microwave devices, depends critically on the resistivity of the SI InP substrate. Because the aggregate experience with the bulk growth and processing of InP substrates, especially Fe-doped boules for SI InP substrates, is less than with GaAs substrates, variation in resistivity occurs from boule-to-boule and within the same boule. To meet the demands of mass production, both measurement and control of resistivity is necessary.

Present techniques of testing resistivity of semiconductor substrates are generally destructive. That is, present techniques of testing resistivity of semiconductor substrates consume the material tested, rendering it unfit for further use. For this reason, the present practice is to sacrifice a very small portion of a large semiconductor substrate wafer in the hopes that the test portion shares the same characteristics of the remaining portions of the wafer, often a very bad and costly assumption. Thus, there exists a need for nondestructive measurement of local resistivity of semiconductor substrates.

U.S. Pat. No. 4,953,983 to Bottka et al., issued Sep. 4, 1990, discloses an apparatus and method for nondestructive measurement of local carrier concentration and bandgap in a semiconductor using photoreflectance. However, U.S. Pat. No. 4,953,983 does not address the need for nondestructive measurement of local resistivity of semiconductor substrates.

SUMMARY OF THE INVENTION

Accordingly, it is an object of the present invention to enable one to non-destructively measure local resistivity of semiconductors.

Another object of the present invention is to achieve the foregoing quickly, simply, inexpensively and reliably.

Yet another object of the present invention is to achieve the foregoing before fabrication of complicated electronic and optoelectronic devices on semiconductor substrates.

Still another object of the present invention is to achieve the foregoing by non-destructive photoreflective techniques.

These and other objects of the present invention are accomplished by a method for measuring resistivity of a preselected portion of a semiconductor, the method comprising the steps of: illuminating the preselected portion of the semiconductor with a first substantially monochromatic light of a first preselected photon energy; selectively illuminating the preselected portion of the semiconductor with a second substantially monochromatic light of an energy sufficient to cause electron-hole generation in the preselected portion of the semiconductor; measuring a change in reflectance of the first substantially monochromatic light from the preselected portion of a semiconductor responsive to the step of selectively illuminating; recording the change in reflectance; recording a photoreflectance line-shape by repeating the steps of illuminating, selectively illuminating, measuring and recording, wherein the step of illuminating is repeated so that the first substantially monochromatic light has a second preselected photon energy different from the first preselected photon energy; calculating a photoreflectance line-shape phase angle based on the photoreflectance line-shape; and determining the resistivity of the preselected portion of the semiconductor based on the photoreflectance line-shape phase angle.

An apparatus according to the present invention includes light sources for illuminating a preselected portion of the semiconductor with first and second light beams, each of a preselected single wavelength, the first light beam bombarding the local portion of the semiconductor with a preselected photon energy, and the second light beam operating to excite the semiconductor by photo injecting carriers. The apparatus also includes a detector to detect a reflectance of the first light beam when the second light beam is off, and again when the second light beam is on. A computation circuit, such as a computer, microprocessor or other suitable computing circuit, operatively connected to the detector, measures a fractional change in reflectance of the first light beam responsive to the second light beam, and records this fractional change in reflectance in a storage area for various values of photon energy of the first light beam, to generate a photoreflectance line-shape. The computer uses the photoreflectance line-shape to calculate a photoreflectance line-shape phase angle, which is used by the computer to determine the resistivity of the preselected portion of the semiconductor.

Besides merely measuring the resistivity of the preselected portion of the semiconductor, in a preferred embodiment of an apparatus according to the present invention, the computer compares the measured resistivity against a standard norm. An annunciator is used to annunciate any unacceptably large deviation from this norm so that a process operator can take appropriate action, for example, discarding the entire substrate as unsatisfactory.

In another preferred embodiment of an apparatus according to the present invention, the apparatus further includes a Joule-Thompson refrigerator that cools the semiconductor, e.g. to a temperature of about 82 K, as the preselected portion of the semiconductor is illuminated by the first and second light beams.

These and other features and advantages of the present invention will be set forth in, or apparent from, the following detailed description and drawings.

BRIEF DESCRIPTION OF THE DRAWINGS

The accompanying drawings illustrate several aspects of the present invention, and together with the detailed description, serve to explain the principles of the present invention. Throughout the drawings, like numerals depict like elements. In the drawings.

DETAILED DESCRIPTION OF THE PREFERRED EMBODIMENT

Figure 1:
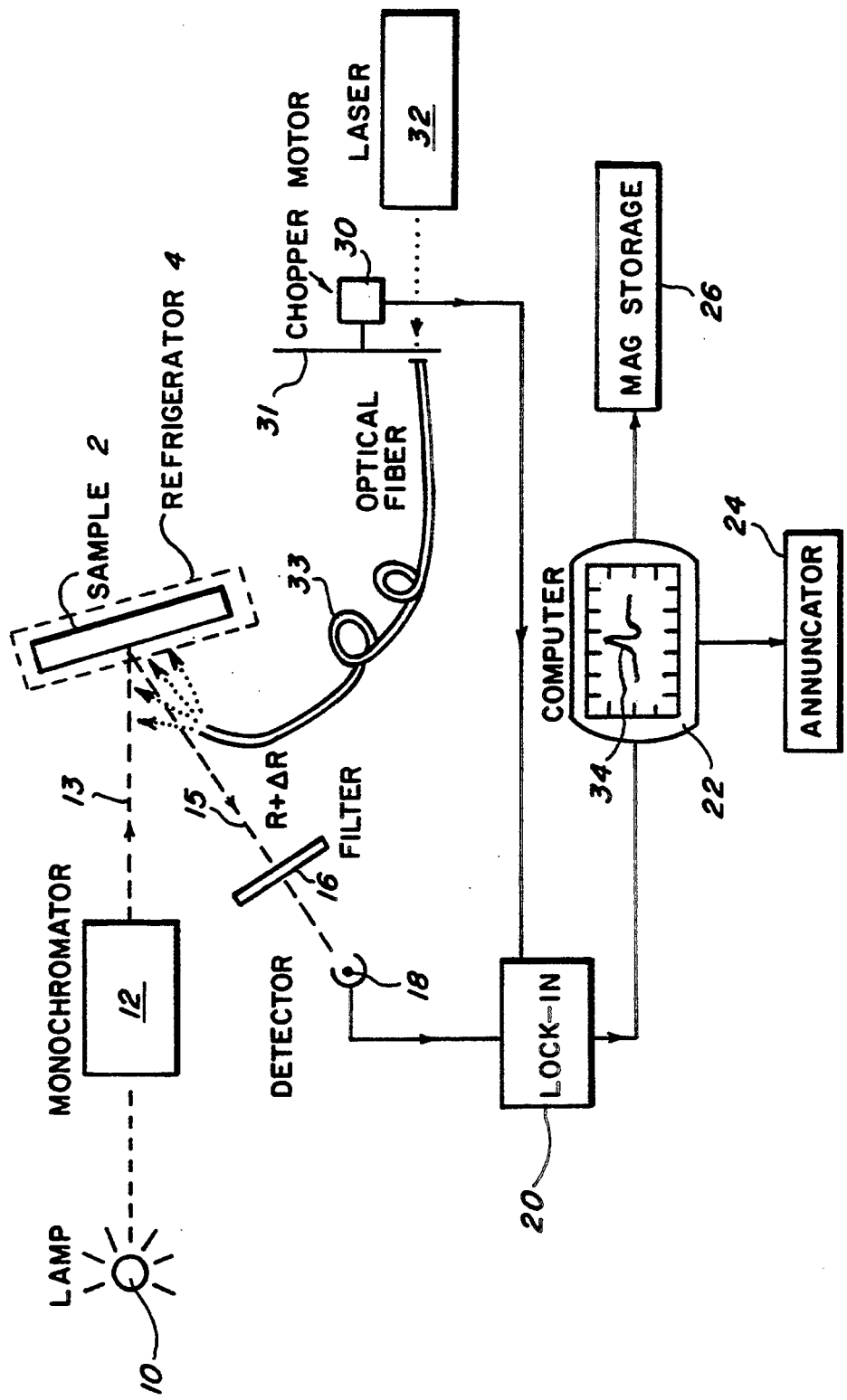
FIG. 1 is a schematic diagram of an embodiment of an apparatus for measuring resistivity of a preselected portion of a semiconductor according to the present invention.

FIG. 1 illustrates schematically a system for practicing the invention. A semiconductor sample 2 is mounted in a conventional Joule-Thompson refrigerator 4 (shown as a dashed line), e.g., MMR Technologies, Inc., Mountain View, Calif., model no. R-2105. Refrigerator 4 includes a window (not shown), through which light can pass. In addition, refrigerator 4 preferably includes a vacuum line (not shown) for maintaining sample 2 under a vacuum, and a temperature controller (not shown) to control the temperature of sample 2. Preferably, the temperature controller of refrigerator 4 can maintain the temperature of sample 2 within the range 80–400 K.

A monochromator 12 filters light from a lamp 10, producing a monochromatic beam of light 13 directed onto sample 2 through the window of refrigerator 4. A laser 32, which also has a monochromatic output, is arranged so that a monochromatic beam of light is directed via an optical fiber or optical coupler 33, through the window of refrigerator 4, and onto the same portion of semiconductor sample 2 that is illuminated by light 13. For example, laser 32 may be an Ar+ laser operating at 514 nm and having a pump beam intensity of 1 mW cm$^{-2}$. A portion of monochromatic light 13 is reflected from the sample 2, as shown at 15, exits through the window of refrigerator 4, and is directed at a filter 16, which filters out light from laser 32. The magnitude of reflected beam 15 is detected by a photodetector 18. Monochromator 12, filter 16 and detector 18 can be any conventional types well known to those skilled in the optics art. Coupler 33 need not be an optical fiber, because any transmission means will do so long as light from laser 32 is directed to illuminate sample 2 as herein described. For example, coupler 33 may alternatively be an optical waveguide, a lens system, or the like.

A screen 31 includes portions opaque to and portions transparent to the output of laser 32. Screen 31 is movably disposed to alternately block and pass the output of laser 32 in response to the movement of a chopper motor 30. In this fashion, chopper motor 30 can be moved at a regular frequency to cause the output of laser 32 to be converted to pulses that are applied to sample 2 at a predetermined chopping rate. A lock-in amplifier 20, also of conventional type, receives synchronization signals from chopper motor 30 and electrical signals from detector 18. In a manner well known in the optics art, lock-in amplifier 20 passes only the electrical signals from detector 18 that alternate in intensity between a low value and a high value in synchronization with the frequency of chopper motor 30. A computation circuit 22, such as a computer, microprocessor or other suitable computing circuitry, receives the electrical signals passed by lock-in amplifier 20, and writes these electrical signals as data into storage area 26.

In operation, with the output of laser 32 blocked by screen 31, the system can be used to measure simple reflectance R as a function of the photon energy of light 13. Lamp 10 and monochromator 12 generate light 13 incident on a portion of sample 2. Sample 2 reflects part of light 13 and absorbs part. The reflected light 15 is incident through filter 16 upon detector 18 which, in detecting the intensity of reflected light 15, also inferentially detects the fraction absorbed by sample 2, and thus the reflectance R of sample 2 when unperturbed by light from laser 32, thereby providing a reflectance baseline against which to make later measurements.

With output of laser 32 passed by screen 31, fiber optical coupler 33 directs the output of laser 32 onto the same portion of sample 2 that is also illuminated by light 13. The photons output by laser 32 are of an energy sufficient to cause electron-hole generation in sample 2, in effect photo-injecting carriers into sample 2. This alters the local carrier concentration of sample 2 in the portion illuminated by the output of laser 32, and this in turn changes the intensity of reflected light 15 by an amount $\Delta R$, so that the sample 2 has a reflectance $(R+\Delta R)$ when perturbed by light from laser 32.

Because, as discussed above, the electrical signals passed by lock-in amplifier 20 alternate in intensity between a low value and a high value in synchronization with the frequency of chopper motor 30, computer 22 calculates the change in reflectance $\Delta R$ by subtracting the low intensity electrical signal value from the high intensity electrical signal value, i.e., $\Delta R = [(R+\Delta R) - R]$. This is step 101 shown in FIG. 5, which is a flow-chart block diagram of steps performed by computer 22. Then, as shown in step 103 of FIG. 5, computer 22 records in its memory the change in reflectance $\Delta R$, along with the reflectance R of sample 2 when unperturbed by light from laser 32, i.e., the low intensity electrical signal value. Computer 22 is preprogrammed in a conventional manner to automatically calculate and record a fractional change in reflectance $\Delta R/R$. These are respectively steps 105 and 107 in FIG. 5.

The photon energy of the light 13 output from monochromator 12 can be selectively varied, and the foregoing procedures repeated to generate a photoreflectance line-shape 34 relating the fractional change in reflectance $\Delta R/R$ to photon energy of light 13, which is then stored in storage area 26. This is step 109 in FIG. 5. Photoreflectance line-shape 34 corresponds to the fractional change in reflectance $\Delta R/R$ responsive to chopped output pulses from laser 32 over the range within which the photon energy of light 13 is varied by monochromator 12. Computer 22, which can be any commercial available computer dedicated in the manner described herein, in its simplest form merely reads data corresponding to photoreflectance line-shape 34 into storage area 26 for later analysis.

Additionally, and preferably, computer 22 can also be programmed to calculate a photoreflectance line-shape phase angle based on the photoreflectance line-shape, and determine the resistivity of the illuminated portion of sample 2 based on the photoreflectance line-shape phase angle (as discussed below). These are respectively steps 111 and 113 in FIG. 5. In this regard, computer 22 can be programmed with equations (as discussed below) for calculating line-shape phase angle, and in turn resistivity. Should computer 22 determine that the resistivity varies by more than a predetermined amount from optimal, computer 22 can cause an annunciator 24, of any conventional type, to indicate this variance. These are respectively steps 115 and 117 in FIG. 5. Annunciator 24 may be a CRT display or a visual or audible alarm, for example. Should computer 22 determine in step 115 that the resistivity varies by less than or equal to the predetermined amount, the computer returns to step 101. This is step 119 in FIG. 5.

The low-temperature photoreflectance line-shape is a measure of the resistivity of the illuminated portion of the semiconductor sample. In the line-shape, the observed change in reflectance ΔR is sensitive to the change in the built-in surface or interfacial electric field of the illuminated portion of the semiconductor sample. The line-shape comes only from regions in the sample which lie within the penetration depth of the probing monochromatic light, i.e., light 13, and which experience an electric field perturbation caused by the output light of laser 32. Any changes in the bulk and/or surface resistivity of the illuminated portion of the semiconductor sample strongly alters the resultant photoreflectance line-shape.

Photoreflectance line-shapes at low temperature consists of elements of an exciton interference effect. The exciton interference model is best understood by starting with the functional form of the photoreflectance line-shape for an exciton:

$$\frac{\Delta R}{R} = Ce^{i\theta}(E - E_X + i\Gamma)^{-m}, \quad (1)$$

where C is an amplitude multiplier, e is the exponential function, i is $(-1)^{\frac{1}{2}}$, $\theta$ is the photoreflectance line-shape phase angle, E is photon energy, $E_X$ is exciton energy, $\Gamma$ is broadening, and m is a parameter that depends on the transition type, which for excitons equals 2. The phase angle $\theta$ varies or rotates the line-shape. In the exciton interference model, the band bending near the surface of the illuminated portion of the semiconductor sample produces an appreciable electric field, and the volume under the surface is broken up into two regions. The first region, beginning next to the surface where x=0, and extending to x<L, has an electric field intense enough to readily ionize excitons. In the second region, where x≧L, the intensity of the electric field is insufficient to ionize excitons. Thus, the optical response of the illuminated portion of the semiconductor sample suffers from a discontinuity at x=L, i.e., at the energy of excitonic transition. This means that the light 13 will interfere with itself as different rays are reflected from the regions bounded by x=0 and x=L. Therefore, phase angle $\theta$ will consist of both an optical path linked component $2\pi L/\lambda_m$, where $\lambda_m$ is the wavelength in the medium, and an additive component which is the natural phase angle of the intrinsic exciton line-shape function. The distance L changes with the temperature of the semiconductor sample and, consequently, the phase angle $\theta$ and the line-shape must also change. Moreover, the distance L also depends on the resistivity of the illuminated portion of the semiconductor sample. The distance L increases as resistivity of the illuminated portion of the semiconductor sample increases. Consequently, phase angle $\theta$ can be used as a measure of the resistivity of the illuminated portion of the semiconductor sample. The phase angle $\theta$ varies smoothly with the resistivity of the illuminated portion of the semiconductor sample.

Fabrication and Measurement Procedures

Semi-insulating (SI) InP:Fe wafers having a 2" diameter were cleaved into small pieces, approximately 0.5 cm$^2$ for use as samples in the above-described system. All of the samples were cleaned and etched before being placed in the Joule-Thompson refrigerator 4. The following cleaning procedure was used: (1) each sample was subjected to a 5 minute detergent degrease in an ultrasonic cleaner, followed by a rinse in deionized water; and (2) then each sample was soaked in trichloroethylene, acetone and methanol, rinsed in deionized water and blown dry using nitrogen. The following etching procedure was used: each sample was subjected to a 4–8 minute dip in a 0.5% (by volume) bromine methanol solution, rinsed in methanol and deionized water, and blown dry using nitrogen. The 300 K etch rate was 1 μm/min. Afterwards, the samples were mounted in refrigerator 4. The photoreflectance measurements were made immediately after etching the samples to minimize the changes in surface chemistry due to exposure to the ambient. The photoreflectance measurements were made near the fundamental absorption edge of InP. A 514 nm Ar+ laser was used as laser 32, and the pump beam intensity was 1 mW cm$^{-2}$. Room-temperature measurements of Hall resistivity were performed on the samples or on adjacent areas using the Van der Pauw technique. The resistivity measurement of the SI InP samples varied from 2.3 to 230 MΩ cm and are given in Table I. The measurement error is estimated to be about ±10%.

TABLE I

| Room Temperature Resistivities of SI InP:Fe Samples | |
|---|---|
| Sample No. | Resistivity (Megohm-cm) |
| 1 | 230 |
| 2 | 210 |
| 3 | 140 |
| 4 | 92 |
| 5 | 72 |
| 6 | 21 |
| 7 | 2.3 |

Figure 2:
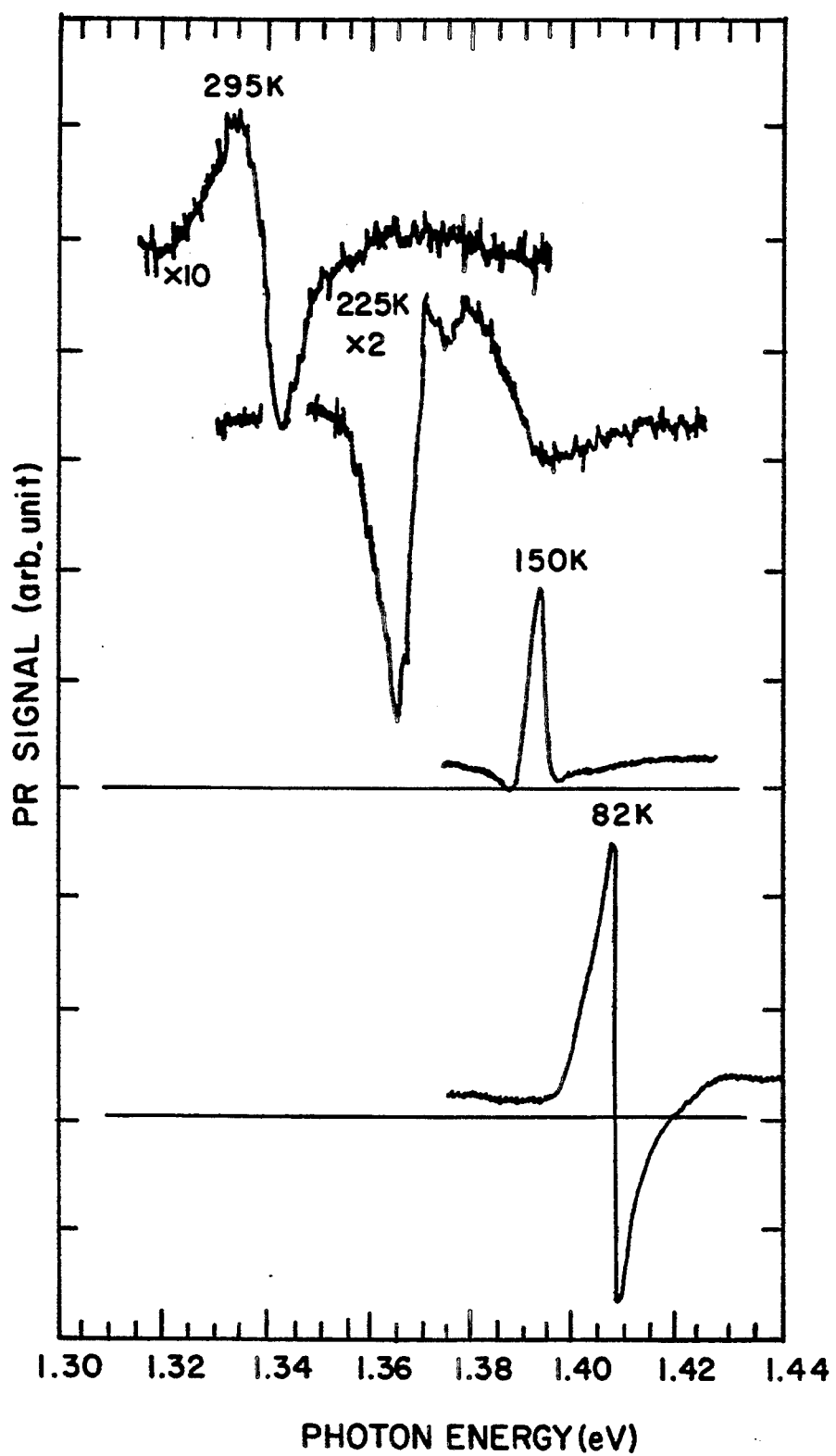
FIG. 2 is a graph of photoreflectance line-shape, illustrating the fractional change in reflectance of InP sample No. 4 versus photon energy at various temperatures.

FIG. 2 shows the photoreflectance line-shape of sample No. 4 at various temperatures. The line-shape was found to change continuously between the temperatures displayed in FIG. 2. The low-temperature line-shapes arise from the exciton interference effect. Near 225 K, an additional structure can be observed on the high-energy side of the line-shape. The origin of this additional structure is probably due to a Franz-Keldysh oscillation because it contributes mainly to the high-energy portion of the signal.

Evidence that the low-temperature photoreflectance line-shapes shown in FIG. 2 are due to the exciton interference effect is as follows. First, the line-shapes are very narrow, of the order of 2 meV at 82 K, strongly suggesting an excitonic and not a band-to-band origin.

Second, the energy associated with the line-shapes is consistent with the free exciton in InP:Fe. Third, the line-shape changes in a continuous manner as the temperature is increased from 82 K, a change that can not occur with band-to-band transitions.

As discussed above, the behavior of the line-shapes shown in FIG. 2 as a function of temperature is explained by the exciton interference model. Fits of the line-shapes of FIG. 2 using Equation (1) indicate that the phase angle $\theta$ decreases with increasing temperature. The physics of semiconductors teaches that the distance L decreases as the temperature increases, which would further imply that phase angle $\theta$ decreases. Thus, since the experimental data is in accord with theory, the exciton interference model can be used to describe the photoreflectance response of the SI InP:Fe samples.

Figure 3:
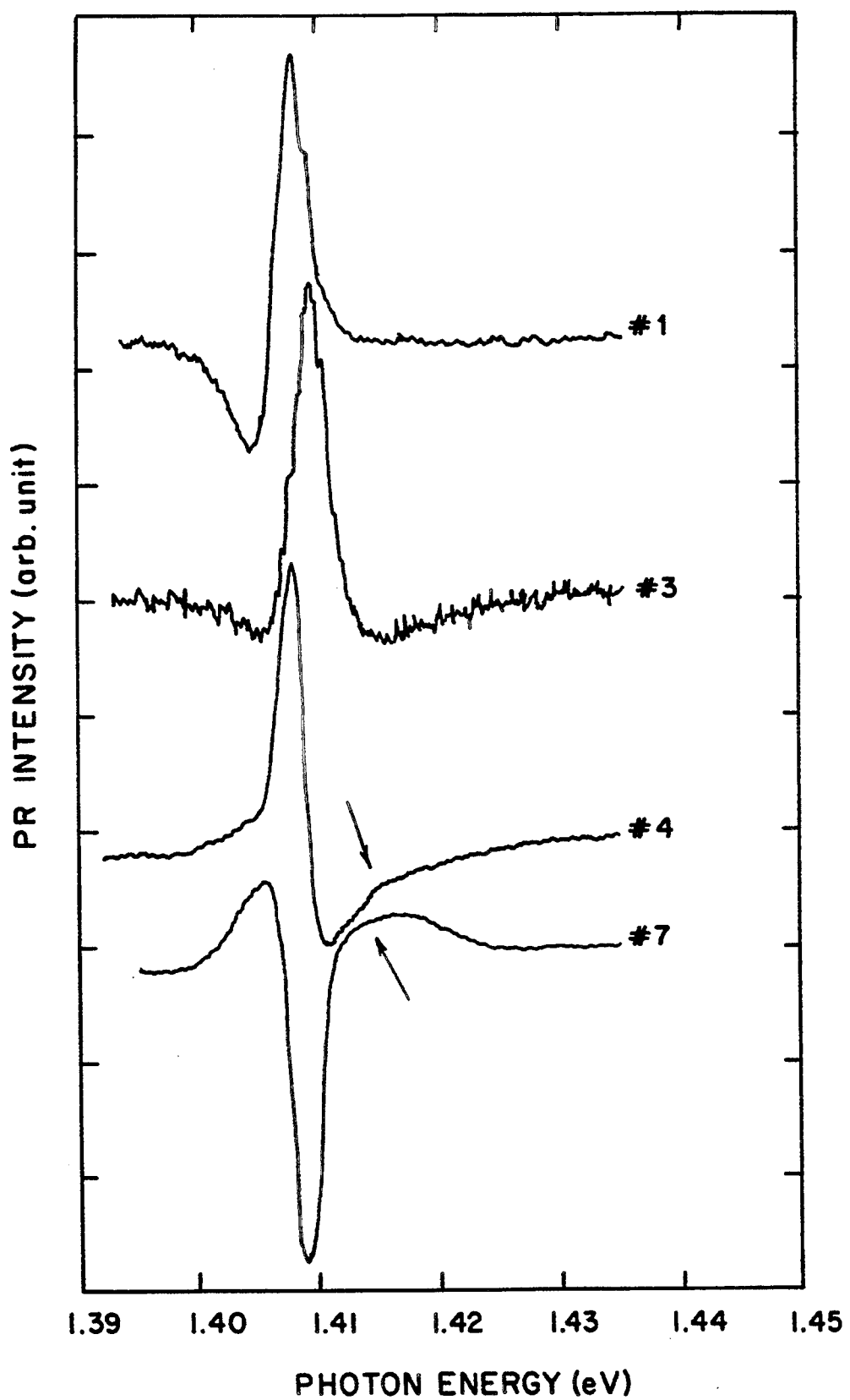
FIG. 3 is a graph of photoreflectance line-shape, illustrating the fractional change in reflectance of InP sample Nos. 1, 3, 4 and 7 versus photon energy at 82 K.

FIG. 3 shows photoreflectance line-shapes of sample Nos. 1, 3, 4 and 7 at 82 K. As discussed above, these line-shapes are excitonic in origin. Note that the line-shape of successive spectra change in a regular manner as the resistivity is changed. For example, the line-shape from sample No. 7, which is a low resistivity sample, is more complex than the simple exciton signature. The line-shape of sample No. 7 exhibits a small kink or shoulder on the highenergy side, marked by an arrow. This line-shape resembles a superposition of a narrow exciton structure with a vestige of a Franz-Keldysh oscillation. Only the low-resistivity samples showed this kind of shouldered line-shape. Also, the line-shapes from low-resistivity samples had enhanced signal intensities as compared to the high-resistivity samples. These observations were substantially replicated at 150 K.

The photoreflectance line-shapes of sample Nos. 1-7 at 82 K were fit to Equation (1). From so fitting the line-shapes, $E_x$ was measured to be 1.408(2) eV for all samples. Also, from fitting the line-shapes, the values of phase angle $\theta$ were found, with an estimated error of ±5°. Preferably, computer 22 is used to fit the line-shapes by Equation (1), and thereby calculate phase angle $\theta$. This corresponds with step 111 of FIG. 5. Alternatively, computer 22 may merely write the data corresponding to the line-shapes into storage area 26 for later analysis by another computer, i.e. end processing within computer 22 at step 109 in FIG. 5.

Figure 4:
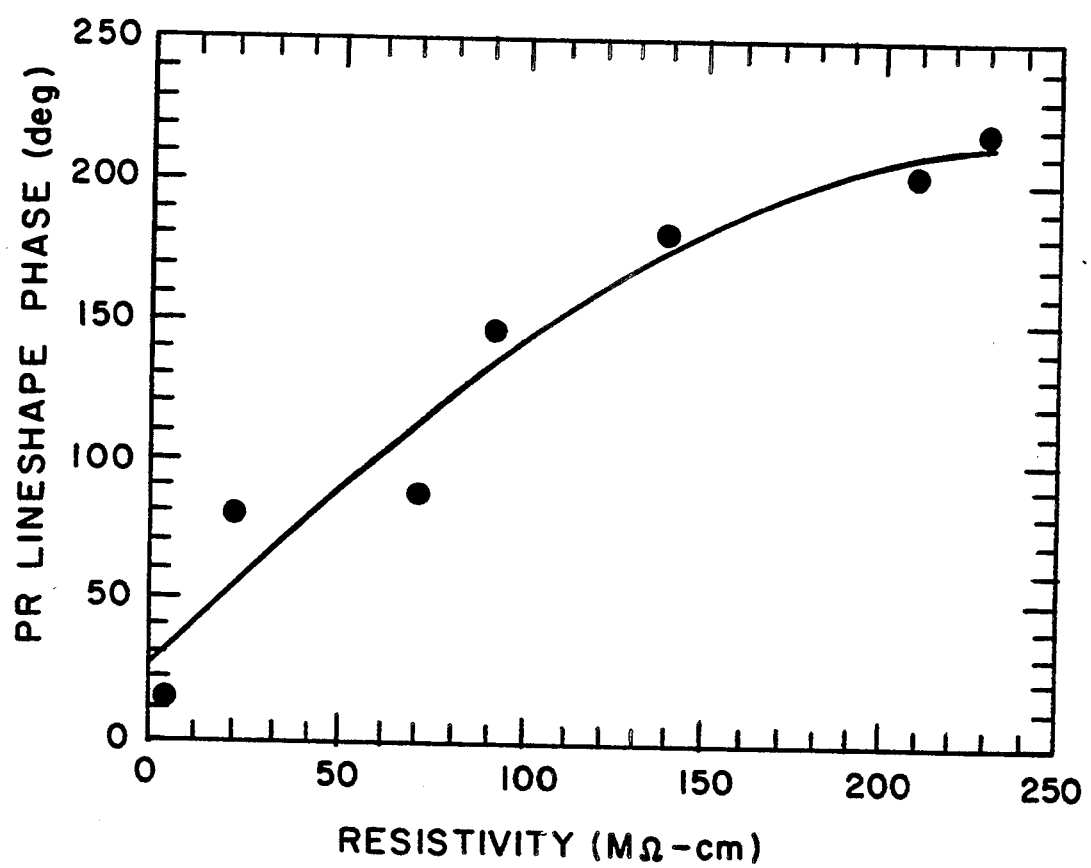
FIG. 4 is a graph illustrating line-shape phase angle at 82 K versus Hall resistivity at room-temperature for InP sample Nos. 1–7.

FIG. 4 is a graph, illustrating photoreflectance line-shape phase angle $\theta$ versus Hall resistivity $\rho$ for sample Nos. 1-7. As can be seen, phase angle $\theta$ varies smoothly with Hall resistivity $\rho$. Thus, FIG. 4 can be used to determine the Hall resistivity of a SI InP:Fe sample. By calculating the phase angle $\theta$ of a SI InP:Fe sample, the solid line in FIG. 4 is used to determine the corresponding Hall resistivity of the sample. In FIG. 4, the solid line has the form:

$$\rho = 5.6 + 4.0 \times 10^{-3}\theta + 4.6 \times 10^{-3}\theta^2, \qquad (2)$$

where Hall resistivity $\rho$ is in M$\Omega$ cm and phase angle $\theta$ is in degrees. Computer 22 may be programmed with Equation (2) to determine Hall resistivity based on phase angle $\theta$.

The line-shapes for sample No. 4 shown in FIG. 2 and FIG. 3 were taken from two different locations of the wafer. In FIG. 2, the line-shape is from the edge region of the wafer. In FIG. 3, the line-shape is from the center region of the wafer. The slight difference in phase angle $\theta$ between these two line-shapes corresponds to about 20 M$\Omega$ cm. This may represent a real variation in resistivity or may merely represent experimental error.

A simple physical model may be employed to understand the resistivity results. The surface Fermi level of ambient exposed InP lies about 0.16 eV below the surface conductionband minimum at 300 K and the surface thereof is in an accumulated state. This condition probably persists at 82 K, albeit changed slightly from 0.16 eV. Samples with higher resistivity will have a larger difference between the bulk Fermi level and the surface conduction-band minimum than samples with lower resistivity. Thus, high resistivity samples will have more band bending measured with respect to the surface, and hence a higher surface electric field. A higher surface electric field translates into an ionizing electric field of greater extent, and hence a larger value of distance L than the lower resistivity samples. This means that, assuming the exciton interference model, the higher resistivity samples will exhibit a larger phase angle $\theta$ than the lower resistivity samples, as shown in FIG. 4, because the optical path length will be larger.

Any semiconductor which acts similarly to InP, that is, has an accumulated surface, i.e., downward bending conduction band, will exhibit a similar phase angle/resistivity relationship, albeit scaled to different values. Semiconductors having depleted surfaces will also exhibit the same relationship. Semiconductors whose surfaces are sufficiently flat-band, like semi-insulating GaAs, will not exhibit this relationship.

Figure 5:
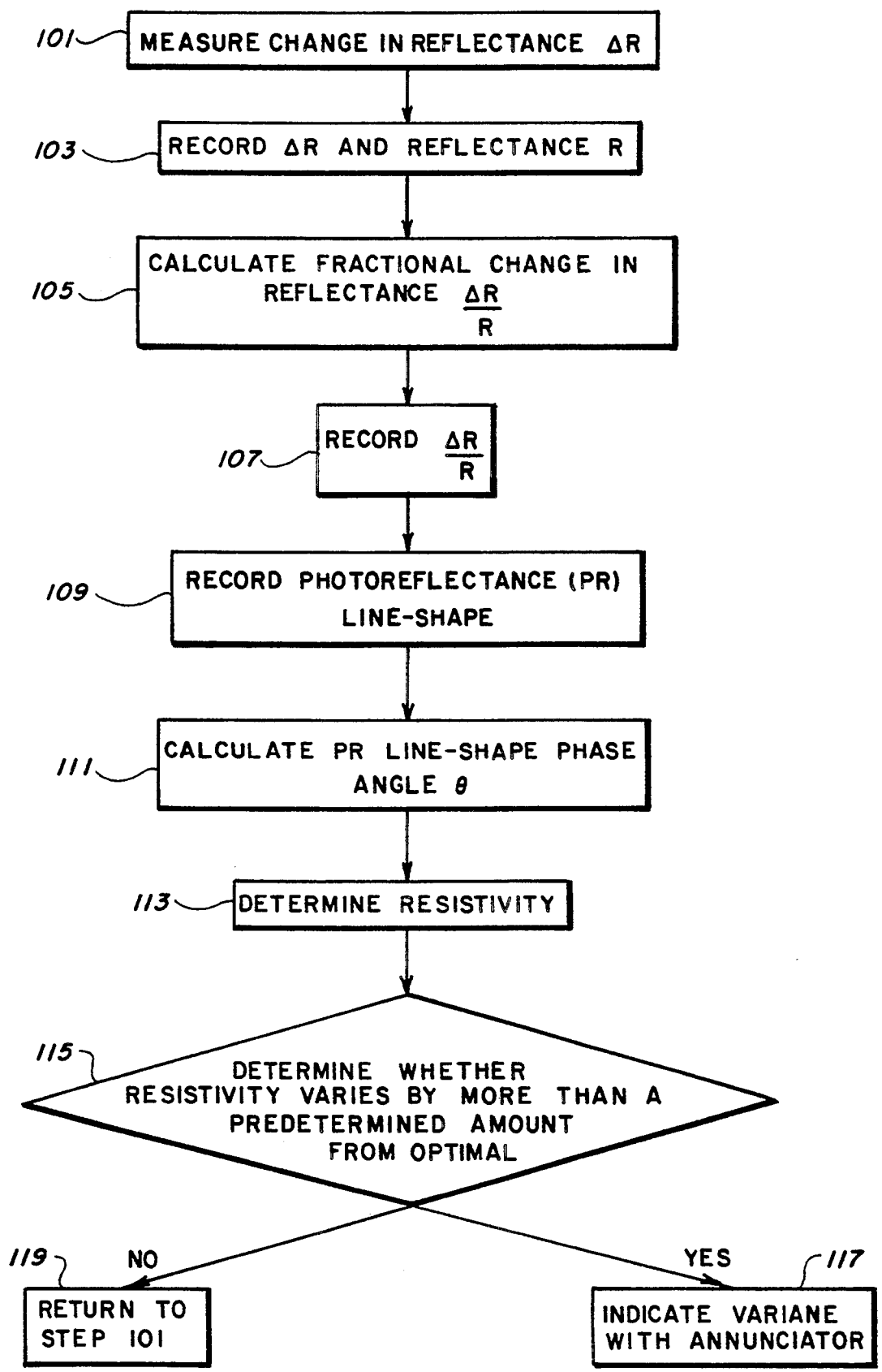
FIG. 5 is a flow-chart block diagram of steps perforated by the computer of the embodiment shown in FIG. 1.
Figure 6:
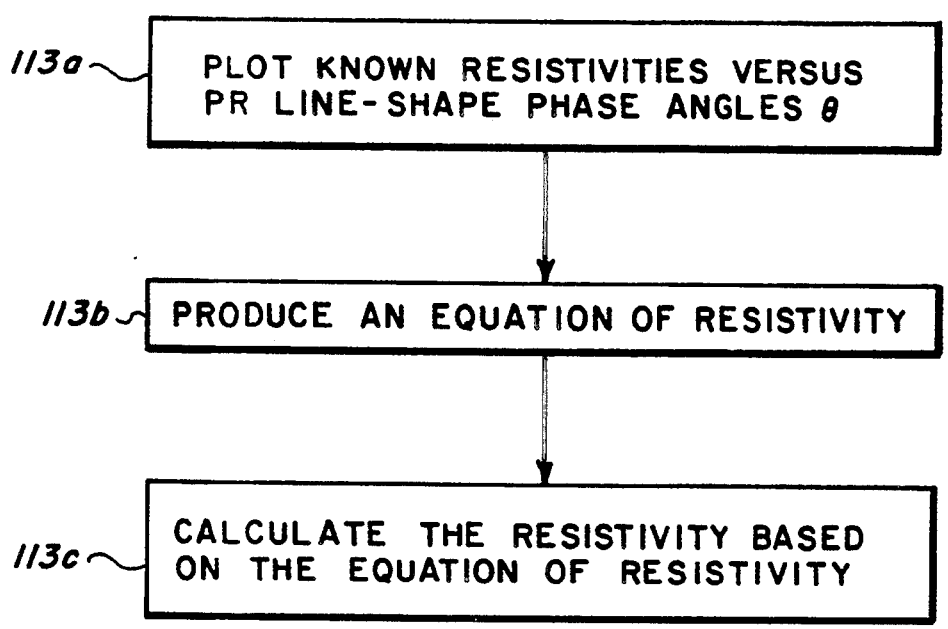
FIG. 6 is a flow-chart block diagram of sub-steps of the step of determining resistivity shown in FIG. 5.

FIG. 6 is a flow-chart block diagram of sub-steps of step 113 shown in FIG. 5. Since experimental apparatus and samples will differ from application to application, samples of known resistivity should be measured to produce a plot such as the one shown in FIG. 4. This plot is then fitted, producing an equation of resistivity as a function of phase angle. The equation can then be used to find the resistivity of unknown samples from measurements of the phase angle. Each of these sub-steps may be accomplished manually or, preferably, by computer 22, as respectively shown in steps 113a–113c of FIG. 6.

The contactless, non-destructive nature of the present invention promises to be of great utility to the electronic and optoelectronic device industry. Measurements could be performed before growth of epitaxial layers or even in-situ as a way of controlling the performance of the product. For example, very high frequency device operation depends on the resistance of the substrate. InP substrates could be preselected for growth, whereby only those showing the highest and most uniform resistivities would be used. Moreover, the present invention quickly, simply, inexpensively and reliably provides a non-destructive measure of local resistivity of semiconductors.

Numerous modifications and adaptations of the present invention will be apparent to those skilled in the art. For example, the probing monochromatic light could be raster scanned across the surface of the semiconductor sample to map the resistivity thereof. Also, instead of photo-injecting carriers into the semiconductor sample using laser 32, other means for causing electron-hole generation could be used, e.g., by selectively applying an electric bias or magnetic field to the semiconductor sample. Thus, it is intended by the following claims to cover all such modifications and adaptations which fall within the true spirit and scope of the invention.

What is claimed is:

1. A method for measuring resistivity of a preselected portion of a semiconductor, said method comprising the steps of:
　　illuminating the preselected portion of the semiconductor with a first substantially monochromatic light of a first preselected photon energy;
　　selectively illuminating the preselected portion of the semiconductor with a second substantially monochromatic light of an energy sufficient to cause electron-hole generation in the preselected portion of the semiconductor;
　　wherein said steps of illuminating, selectively illuminating are carried out at or about 82 K;
　　measuring a change in reflectance of the first substantially monochromatic light from the preselected portion of the semiconductor responsive to said step of selectively illuminating;
　　recording said change in reflectance;
　　recording a photoreflectance line-shape by repeating said steps of illuminating, selectively illuminating, measuring and recording, wherein said step of illuminating is repeated so that said first substantially monochromatic light has a second preselected photon energy different from said first preselected photon energy;
　　calculating a photoreflectance line-shape phase angle based on said photoreflectance line-shape;
　　determining the resistivity of the preselected portion of the semiconductor based on said photoreflectance line-shape phase angle, and
　　wherein said step of determining the resistivity of the preselected portion of the semiconductor comprises the substep of:
　　　　calculating Hall resistivity $\rho$ of the preselected portion of the semiconductor by the equation $$\beta = 5.6 + 4.0 \times 10^{-3}\Theta + 4.6 \times 10^{-3}\Theta^2$$

where $\Theta$ is said photoreflectance line-shape phase angle.

2. A method as recited in claim 1, wherein said step of calculating said photoreflectance line-shape phase angle comprises the sub-step of:
　　fitting said photoreflectance line-shape to the equation $$\frac{\Delta R}{R} = Ce^{i\theta}(E - E_X + i\Gamma)^{-m},$$

where $\Delta R$ is said change in reflectance, R is a reflectance of said first substantially monochromatic light from the preselected portion of the semiconductor when the preselected portion of the semiconductor is not illuminated by said second substantially monochromatic light, C is an amplitude multiplier, e is the exponential function, i is $(-1)^{\frac{1}{2}}$, $\theta$ is said photoreflectance line-shape phase angle, E is photon energy, $E_X$ is exciton energy, $\Gamma$ is broadening, and m is a transition parameter.

3. A method as recited in claim 1, wherein said step of determining the resistivity of the preselected portion of the semiconductor comprises the sub-step of:
　　making a plot of known resistivities of sample semiconductors versus corresponding photoreflectance line-shape phase angles of said sample semiconductors.

4. A method as recited in claim 1, wherein the semiconductor has an accumulated surface.

5. A method as recited in claim 1, wherein the semiconductor comprises InP.

6. A method as recited in claim 1, further comprising the step of:
　　determining if the resistivity of the preselected portion of the semiconductor varies by more than a preselected amount from a preselected value.

7. A method for measuring resistivity of a preselected portion of a semiconductor, said method comprising the steps of:
　　illuminating the preselected portion of the semiconductor with a first substantially monochromatic light of a first preselected photon energy;
　　selectively illuminating the preselected portion of the semiconductor with a second substantially monochromatic light of an energy sufficient to cause electron-hole generation in the preselected portion of the semiconductor;
　　measuring a change in reflectance of the first substantially monochromatic light from the preselected portion of the semiconductor responsive to said step of selectively illuminating;
　　recording said change in reflectance;
　　recording a photoreflectance line-shape by repeating said steps of illuminating, selectively illuminating, measuring and recording, wherein said step of illuminating is repeated so that said first substantially monochromatic light has a second preselected photon energy different from said first preselected photon energy;
　　calculating a photoreflectance line-shape phase angle based on said photoreflectance line-shape;
　　determining the resistivity of the preselected portion of the semiconductor based on said photoreflectance line-shape phase angle; and
　　wherein said step of determining the resistivity of the preselected portion of the semiconductor comprises the substeps of:
　　making a plot of known resistivities of sample semiconductors versus corresponding photoreflectance line-shape phase angles of said sample semiconductors;
　　producing an equation of resistivity as a function of photoreflectance line-shape phase angle by fitting said plot to said equation; and
　　calculating the resistivity of the preselected portion of the semiconductor based on said equation and said photoreflectance line-shape phase angle.

8. A method for measuring resistivity of a preselected portion of a semiconductor, said method comprising the steps of:
　　illuminating the preselected portion of the semiconductor with a first substantially monochromatic light of a first preselected photon energy;
　　selectively illuminating the preselected portion of the semiconductor with a second substantially monochromatic light of an energy sufficient to cause electron-hole generation in the preselected portion of the semiconductor;
　　cooling the semiconductor to a temperature of less than or equal to 150 K during said steps of illuminating and selectively illuminating;
　　measuring a change in reflectance of the first substantially monochromatic light from the preselected portion of the semiconductor responsive to said step of selectively illuminating;
　　recording said change in reflectance;
　　recording a photoreflectance line-shape by repeating said steps of illuminating, selectively illuminating, measuring and recording, wherein said step of illuminating is repeated so that said first substantially monochromatic light has a second preselected photon energy different from said first preselected photon energy;

calculating a photoreflectance line-shape phase angle based on said photoreflectance line-shape; and determining the resistivity of the preselected portion of the semiconductor based on said photoreflectance line-shape phase angle.

9. A method for measuring resistivity of a preselected portion of a semiconductor, said method comprising the steps of:

illuminating thepreselected portion of the semiconductor with a first substantially monochromatic light of a first preselected photon energy;

selectively illuminating the preselected portion of the semiconductor with a second substantially monochromatic light of an energy sufficient to cause electron-hole generation in the preselected portion of the semiconductor;

cooling the semiconductor to a temperature at or about 82 K during said steps of illuminating and selectively illuminating;

measuring a change in reflectance of the first substantially monochromatic light from the preselected portion of the semiconductor responsive to said step of selectively illuminating;

recording said change in reflectance;

recording a photoreflectance line-shape by repeatinq said steps of illuminating, selectively illuminating, measuring and recording, wherein said step of illuminating is repeated so that said first substantially monochromatic light has a second preselected photon energy different from said first Dreselected photon energy;

calculating a photoreflectance line-shape phase angle based on said photoreflectance line-shape; and determining the resistivity of the preselected portion of the semiconductor based on said photoreflectance line-shape phase angle.

10. A method for measuring resistivity of a preselected portion of a semiconductor, said method comprising the steps of:

illuminating the preselected portion of the semiconductor with a first substantially monochromatic light of a first preselected photon energy;

selectively illuminatinq the preselected portion of the semiconductor with a second substantially monochromatic light of an energy sufficient to cause electron-hole generation in the preselected portion of the semiconductor;

cooling the semiconductor to a temperature at or about 82 K during said steps of illuminating and selectively illuminating;

measuring a change in reflectance of the first substantially monochromatic light from the preselected portion of the semiconductor responsive to said step of selectively illuminating;

recording said change in reflectance;

recording photoreflectance line-shape by repeating said steps of illuminating, selectively illuminating, measuring and recording, wherein said step of illuminating is repeated so that said first substantially monochromatic light has a second preselected photon energy different from said first preselected photon energy;

calculating a photoreflectance line-shape phase angle based on said photoreflectance line-shape;

determining the resistivity of the preselected portion of the semiconductor based on said photoreflectance line-shape phase angle; and annunciating when the resistivity of the preselected portion of the semiconductor varies by more than said preselected amount from said preselected value.

11. An apparatus for measurinq resistivity of a preselected portion of a semiconductor comprising;

means for detecting a photoreflectance line-shape of the preselected portion of the semiconductor at a preselected temperature and along a preselected range of photon energies; and determining means for calculating a photoreflectance line-shape phase angle based on said reflectance line-shape and for determining the resistivity of the preselected portion of the semiconductor based on said photoreflectance line-shape phase angle;

wherein the preselected temperature is at or about 82 K, and wherein said means for determininq includes a computer for calculating Hall resistivity, $\rho$, of the preselected portion of the semiconductor by the equation $$\rho = 5.6 + 4.0 \times 10^{-3}\Theta + 4.6 \times 10^{-3}\Theta^2$$

where $\Theta$ is said photoreflectance line-shaped phase angle.

12. An apparatus as recited in claim 11, wherein said determining means includes a computation circuit for fitting said photoreflectance line-shape to the equation $$\frac{\Delta R}{R} = Ce^{i\theta}(E - E_X + i\Gamma)^{-m}$$

where $\Delta R$ is said change in reflectance, R is a reflectance of said first substantially monochromatic light from the preselected portion of the semiconductor when the preselected portion of the semiconductor is not illuminated by said second substantially monochromatic light, C is an amplitude multiplier, e is the exponential function, i is $(-1)^{\frac{1}{2}}$, $\theta$ is said photoreflectance line-shape phase angle, E is photon energy, $E_X$ is exciton energy, F is broadening, and m is a transition parameter.

13. An apparatus as recited in claim 11, wherein said determining means includes a computing circuit for making a plot of resistivities of sample semiconductors versus corresponding known photoreflectance line-shape phase angles of said sample semiconductors.

14. An apparatus as recited in claim 11, wherein said determining means includes a computing circuit for making a plot of known resistivities of sample semiconductors versus corresponding photoreflectance line-shape phase angles of said semiconductors, for producing an equation of resistivity as a function of photoreflectance line-shape phase angle by fitting said plot to said equation, and for calculating the resistivity of the preselected portion of the semiconductor based on said equation and said photoreflectance line-shape phase angle.

15. An apparatus as recited in claim 11, wherein the semiconductor has an accumulated surface.

16. An apparatus as recited in claim 11, wherein the semiconductor comprises InP.

17. An apparatus as recited in claim 11, wherein said determining means includes a computing circuit for determining if the resistivity of the preselected portion of the semiconductor varies by more than a preselected amount from a preselected value.

18. An apparatus for measuring resistivity of a preselected portion of a semiconductor comprising:
  means for detecting a photoreflectance line-shape of the preselected portion of the semiconductor at a preselected temperature and along a preselected range of photon energies; and
  determining means for calculating a photoreflectance line-shape phase angle based on said reflectance line-shape and for determining the resistivity of the preselected portion of the semiconductor based on said photoreflectance line-shape phase angle; and
  means for cooling the semiconductor to said selected temperature, said preselected temperature being more than or equal to 150 K.

19. An apparatus for measuring resistivity of a preselected portion of a semiconductor comprising;
  means for detecting a photoreflectance line-shape of the preselected portion of the semiconductor at a preselected temperature and along a preselected range of photon enerqies; and
  determining means for calculating a photoreflectance line-shape phase angle based on said reflectance line-shape and for determining the resistivity of the preselected portion of the semiconductor based on said photoreflectance line-shape phase angle; and
  means for cooling the semiconductor to said predetermined temperature, said predetermined temperature being at or about 82 K.

20. An apparatus for measuring resistivity of a preselected portion of a semiconductor comprising;
  means for detecting a photoreflectance line-shape of the preselected portion of the semiconductor at a preselected temperature and along.a..preselected range of photon energies; and
  determining means for calculating a photoreflectance line-shape phase angle based on said reflectance line-shape and for determining the resistivity of the preselected portion of the semiconductor based on said photoreflectance line-shape phase angle; and
  means for coolinq the semiconductor to said preselected temperature, said preselected temperature being more than or equal to 150 K; and
  means for annunciating when the resistivity of the preselected portion of the semiconductor varies by more than said preselected amount from said preselected value.

* * * * *